(12) United States Patent
Machamer (10) Patent No.: US 9,795,411 B2
(45) Date of Patent: Oct. 24, 2017

(54) FIXATORS FOR BONE STABILIZATION AND ASSOCIATED SYSTEMS AND METHODS

(71) Applicant: GLOBUS MEDICAL, INC., Audubon, PA (US)

(72) Inventor: David Machamer, Glen Mills, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

(21) Appl. No.: 15/058,372

(22) Filed: Mar. 2, 2016

(65) Prior Publication Data

US 2017/0252067 A1    Sep. 7, 2017

(51) Int. Cl.
*A61B 17/62* (2006.01)

(52) U.S. Cl.
CPC .................... *A61B 17/62* (2013.01)

(58) Field of Classification Search
CPC ....... A61B 17/62; A61B 17/66; A61B 17/645; A61B 17/6425; A61B 17/8875; A61B 17/6441; A61B 17/88; A61B 17/848; A61B 17/6466; A61B 17/171; A61B 2017/564; A61B 2017/681; A61B 17/8861
USPC ..... 606/54–59, 96, 104, 105, 267, 309, 916; 602/32–40
See application file for complete search history.

(56) References Cited

U.S. PATENT DOCUMENTS

| | | | | |
|---|---|---|---|---|
| 4,784,125 A | * | 11/1988 | Monticelli | ............. A61B 17/62 606/56 |
| 4,936,843 A | * | 6/1990 | Sohngen | ............ A61B 17/6441 606/54 |
| 5,728,095 A | | 3/1998 | Taylor et al. | |
| 5,746,741 A | | 5/1998 | Kraus et al. | |
| 5,928,230 A | | 7/1999 | Tosic | |
| 6,659,972 B2 | * | 12/2003 | Stamper | .................. A61F 5/055 128/846 |
| 8,858,555 B2 | | 10/2014 | Crozet et al. | |
| 8,945,128 B2 | | 2/2015 | Singh et al. | |
| 8,951,252 B2 | | 2/2015 | Steiner et al. | |
| 2006/0276786 A1 | | 12/2006 | Brinker | |
| 2015/0127093 A1 | * | 5/2015 | Hosmer | ................ A61F 2/2418 623/2.11 |

* cited by examiner

*Primary Examiner* — Pedro Philogene (57) ABSTRACT

The present technology relates generally to ring fixators and associated systems and methods. In some embodiments, for example, a ring fixator assembly comprises a ring configured to surround a fractured bone, a retention device disposed at a first position on the ring, and a tensioner clamp disposed at a second position on the ring. A wire extends between the retention device and the tensioner clamp. The tensioner clamp includes a first screw configured to secure the wire in position with respect to the tensioner clamp and a second screw configured to apply additional tension to the wire.

15 Claims, 7 Drawing Sheets

FIXATORS FOR BONE STABILIZATION AND ASSOCIATED SYSTEMS AND METHODS

TECHNICAL FIELD

The present technology is generally related to fixators for stabilization of fractured bones.

BACKGROUND

For background purposes, a ring fixator is a stabilization device that is used on patients to treat complex and/or open bone fractures. The ring fixator is comprised of pins and wires secured to external scaffolding to provide support to a limb. This allows a bone or joint to be stabilized (e.g., via fusion) during trauma or limb reconstruction.

A ring fixator can be formed by a plurality of rings that are fixed to bone via tensioned pins or wires. The ring fixator can be used, for example, in fractured areas of high severity (e.g., with gunshot wounds), whereby traditional fixators are incapable of stabilizing the tissue. The ring fixators can remain in place until bone or joint stabilization is complete, upon which they can be removed.

SUMMARY

In one aspect of the present invention, a ring fixator assembly is disclosed. The ring fixator assembly includes a ring configured to surround a bone, a retention device disposed at a first position on the ring, a tensioner clamp disposed at a second position on the ring, and a wire extending between the retention device and the tensioner clamp. The tensioner clamp includes a clamping member configured to secure the wire in position with respect to the tensioner clamp and a tensioning member configured to apply tension to the wire.

In another aspect of the present invention, a tensioner clamp for a ring fixator assembly is disclosed. The tensioner clamp includes a central passage configured to receive a wire therein, a clamping member configured to secure the wire in position within the central passage, and a tensioning member configured to apply tension to the wire after the clamping member has secured the wire in position.

DETAILED DESCRIPTION

Figure 1:
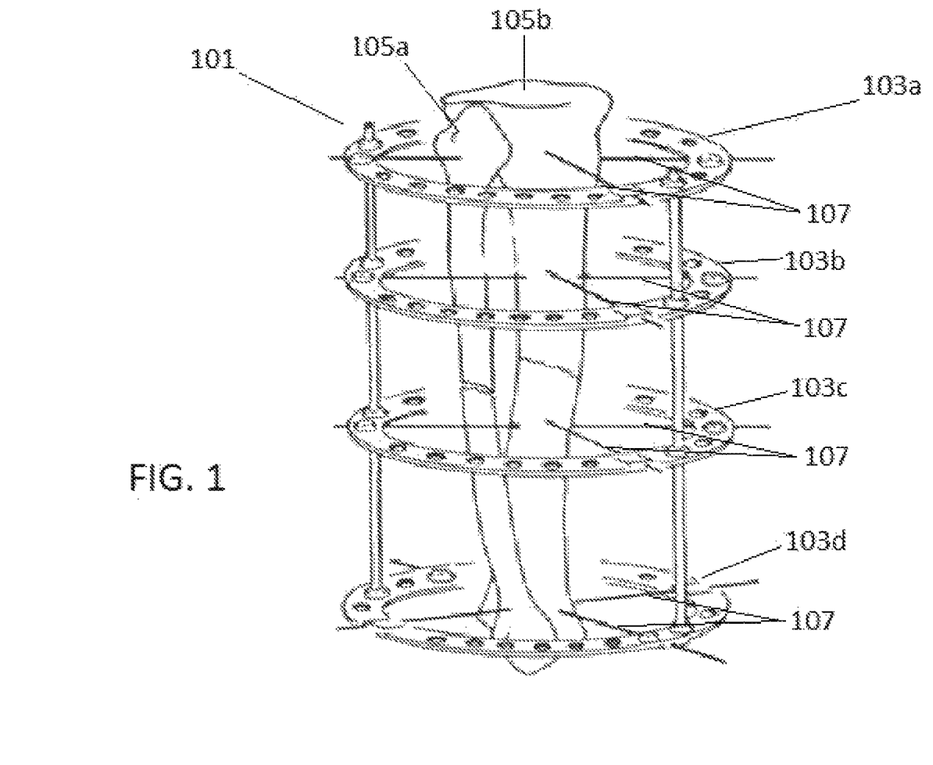
FIG. 1 is a schematic illustration of a ring fixator assembly.

The present disclosure relates to improved ring fixators. An example of a ring fixator is shown in FIG. 1. The ring fixator 101 includes multiple rings 103a-d that surround a patient's fractured bones 105a, 105b. A plurality of wires 107 extend across the individual rings 103a-d, passing through the bones 105a, 105b, thereby providing stability to the fractured bones 105a, 105b while the fractured bones are healed (e.g., via fusion). The ring fixator 101 can be positioned on the patient for as long as necessary until stabilization (e.g., via fusion) is achieved.

As shown in FIG. 1, each of the rings 103a-d of the ring fixator 101 can include one or more wires 107 that are attached to a ring member. To attach the one or more wires 107 to their respective ring member 103a-d, each of the wires would first be clamped to the ring member (e.g., via a clamping instrument). Following attachment, the one or more wires 107 would then be placed in tension (e.g., via a tensioner). These steps would involve two instruments—namely the clamping instrument for attachment and the tensioner for tensioning. The use of two instruments to perform multiple steps can be time consuming in an operation room, as a surgeon would have to first seek out a clamping instrument and then a tensioner for each location on the ring wherein a wire is attached.

Figure 2:
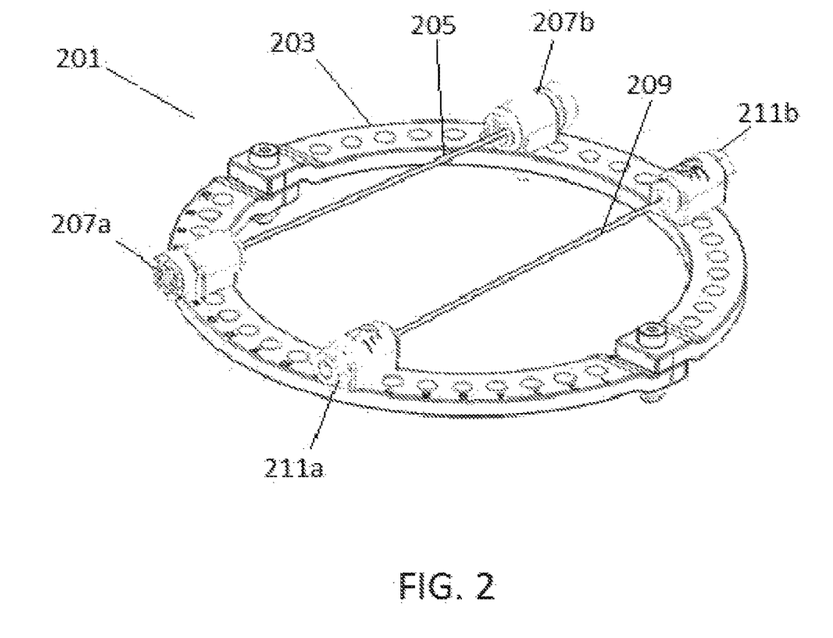
FIG. 2 illustrates a ring fixator including first and second tensioner clamps in accordance with an embodiment of the present technology.

The present disclosure is related to embodiments of an improved ring fixator utilizing a combined clamp and tensioner ("tensioner clamp"), which reduces a need to have both a clamping instrument and a separate tensioning instrument. Advantageously, in some embodiments, a single instrument can be used with the tensioner clamp, thereby saving valuable time in an operating room. FIGS. 2-6 show different embodiments of an improved tensioner clamp in accordance with some embodiments. In particular, as shown in FIG. 2, a ring fixator assembly 201 can utilize one or more types of tensioner clamps. One type of tensioner clamp 207a, 207b is shown attached to wire 205, while a second type of tensioner clamp 211a, 211b is shown attached to wire 209.

FIG. 2 illustrates a ring 203 of a ring fixator assembly 201 ("ring fixator 201") having four tensioner clamps affixed around the perimeter of the ring 203. A first wire 205 extends between two of a first type of tensioner clamp 207a, 207b, while a second wire 209 extends between two of a second type of tensioner clamp 211a, 211b. Each of the tensioner clamps 207 and 211 are configured to both clamp the wires 205 and 209 in place and to apply tension to the wires 205 and 209 after they have been clamped. In some embodiments, a single instrument can be used for both clamping and tensioning, thereby eliminating the need for multiple instruments.

Figures 3A, 3B:
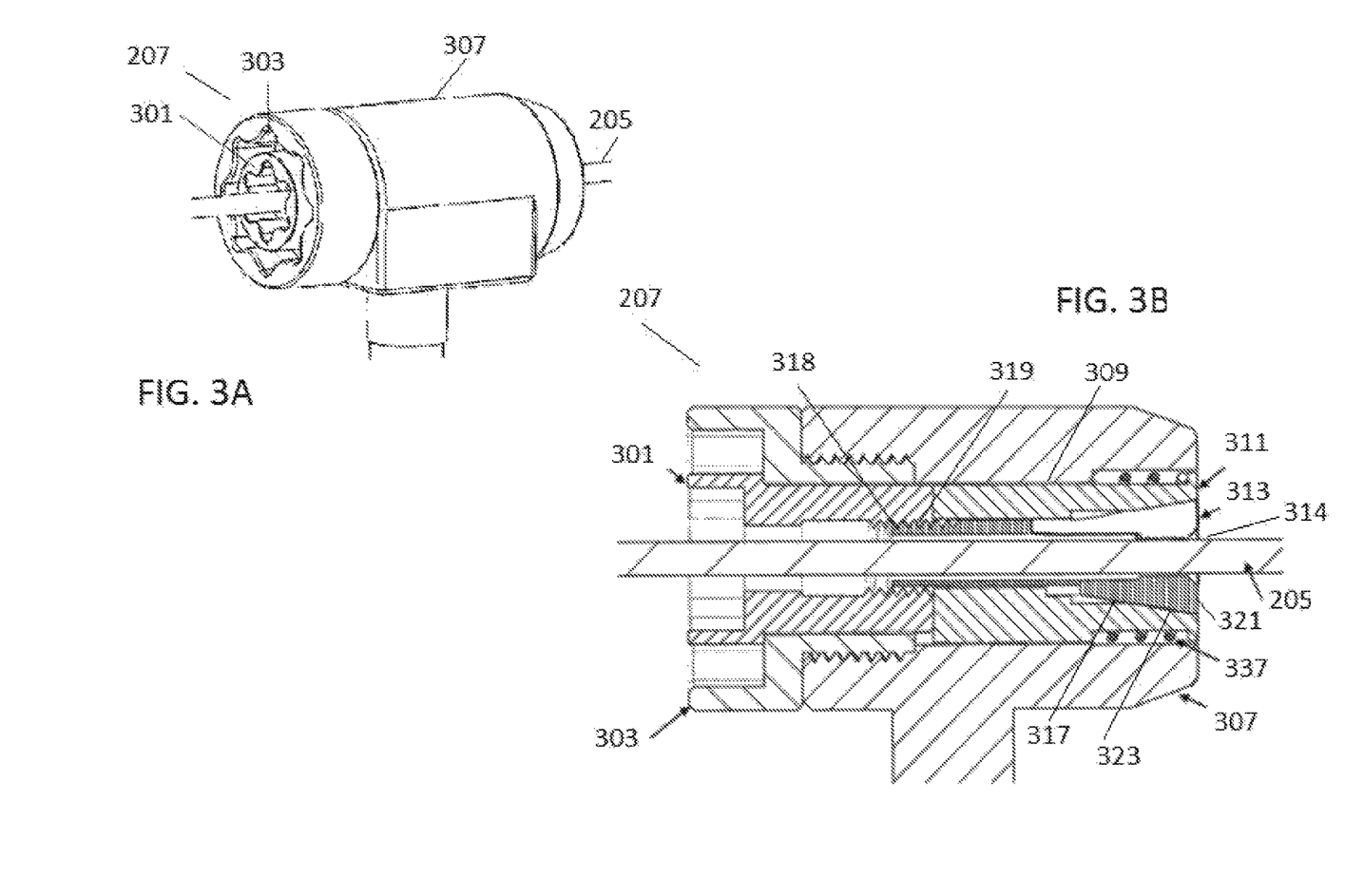
FIGS. 3A-3D illustrate various views of the first tensioner clamp configured in accordance with an embodiment of the present technology.

The first and second tensioner clamps 207 and 211 are described in more detail below. Although the embodiment illustrated in FIG. 2 includes first and second tensioner clamps 207 and 211, in other embodiments the ring fixator may include only one type of tensioner clamp. In addition, in some embodiments the wire can be secured at one end by a simple retention device (e.g., a clamp device that cannot apply additional tension), while the wire is secured at the other end by a tensioner clamp. In additional embodiments, the term retention clamp can apply not only to a clamp that cannot apply additional tension, but also to a tensioner clamp. A first tensioner clamp 207 is shown in FIGS. 3A-3D, while a second tensioner clamp 211 is shown in FIGS. 4A-4C. FIG. 3A is a perspective view of a first tensioner clamp 207 engaging the wire 205 in accordance with some embodiments. As illustrated, the first tensioner clamp 207 includes a clamping screw 301 coaxial with a tensioning screw 303. A first driver (not shown) can be used to rotate the clamping screw 301, which causes a clamping member to secure the inner wire 205. A second driver (not shown) can then be used to rotate the tensioning screw 303, which causes tension to be applied to the inner wire 205. In other embodiments, a single driver can be used to control both the clamping screw 301 and the tensioning screw 303, thereby reducing the need for two separate drivers. In other embodiments, a single instrument can house a first driver for operating the clamping screw 301 and a second driver for operating the tensioning screw 303, thereby advantageously allowing a single instrument to perform both clamping and tensioning.

Figures 3C, 3D:
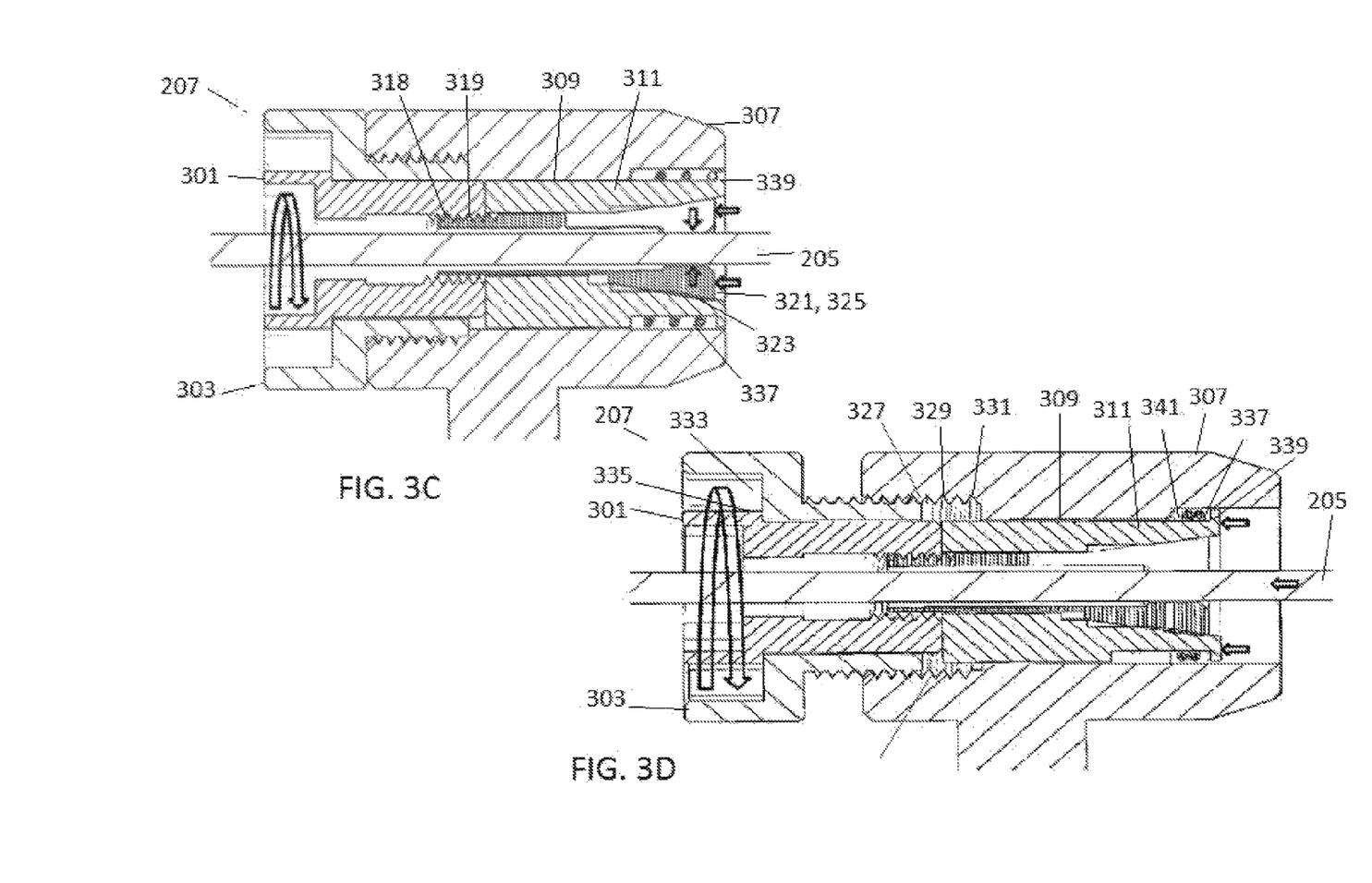
Figure 4A:
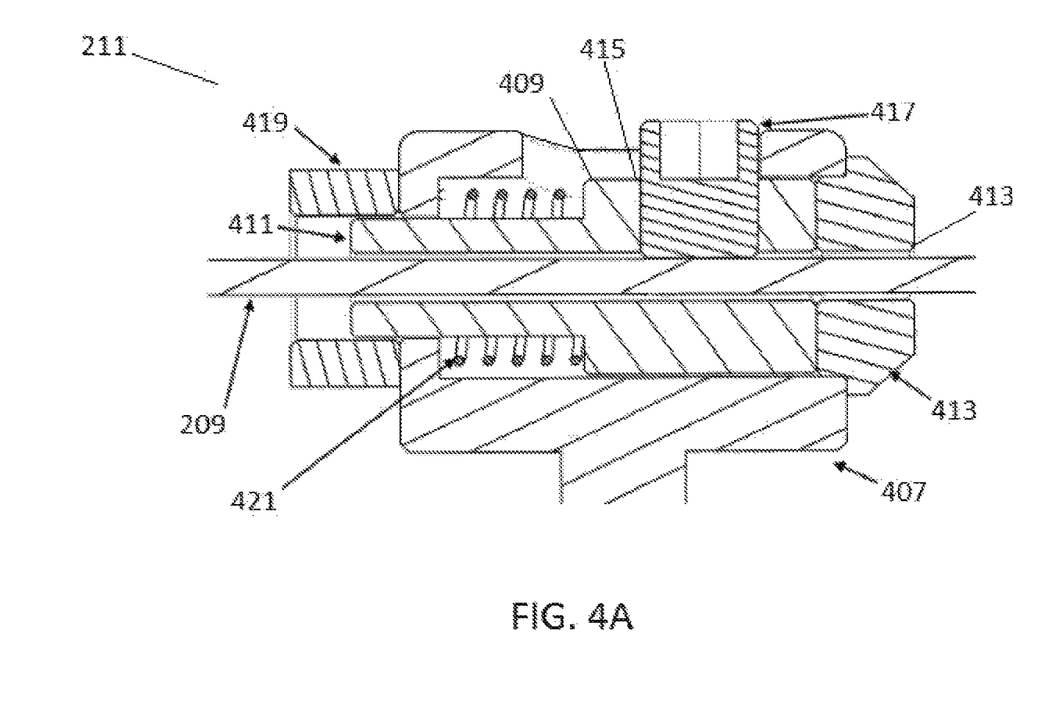
FIGS. 4A-4C illustrate various views of the second tensioner clamp configured in accordance with an embodiment of the present technology.
Figure 4B:
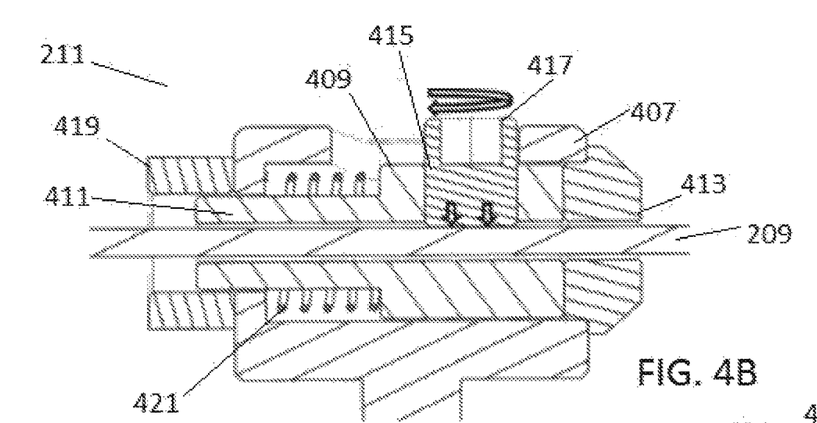
Figure 4C:
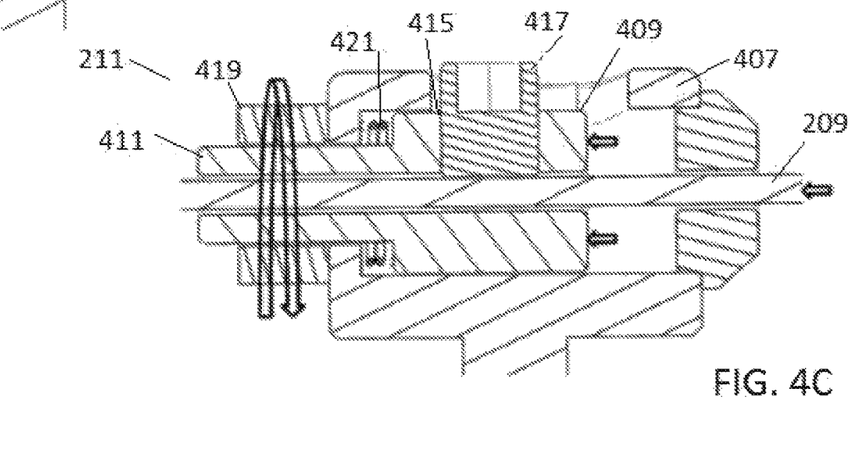

FIGS. 3B-3D illustrate side cross-sectional views of the first tensioner clamp 207 engaged with the wire 205 during different points of operation of the first tensioner clamp 207. In particular, FIG. 3B illustrates the first tensioner clamp 207 prior to clamping the wire 205, FIG. 3C illustrates the first tensioner clamp 207 after clamping the wire 205, and FIG. 3D illustrates the first tensioner clamp 207 after both clamping and tensioning the wire 205.

Referring to FIG. 3B, the first tensioner clamp 207 includes an outer housing 307. The housing 307 can be configured to be fixedly attached to a ring of a ring fixator. Within the housing 307 is a clamping assembly 309 which clamps the wire 205 in place in response to rotation of the clamping screw 301. The clamping assembly 309 includes a collet housing 311 received within the outer housing 307 and a collet 313 received within the collet housing 311. The collet 313 has a central opening 314 to receive the wire 205 therein, and includes a proximal end portion 315 and a distal end portion 317 opposite to the proximal end portion 315. The proximal end portion 315 includes threads 318 that are configured to engage with corresponding threads 319 of the clamping screw 301. The distal end portion 317 includes a compressible member 321 that engages with an angled surface 323 of the collet housing 311.

As illustrated in FIG. 3C, during operation, the clamping screw 301 is rotated, causing the collet 313 to be retracted relative to the collet housing 311. During this retraction, the compressible member 321 of the collet 313 engages with the angled surface 323 of the collet housing 311, thereby causing the compressible member 321 to press inwardly onto the wire 205, effectively clamping the wire 205 in place. In the illustrated embodiment, the compressible member 321 takes the form of a plurality of flared portions 325 separated by gaps such that these flared portions can be drawn inwardly radially together by engagement with the angled surface 323 of the collet housing 311 until the flared portions 325 come into contact with the wire 205.

Once the wire 205 has been clamped into position by rotation of the clamping screw 301, the wire 205 can be tensioned. Referring to FIG. 3D, the tensioning screw 303 includes distal threads 327 that are threadably engaged with corresponding threads 329 on an interior surface 331 of the housing 307. Rotation of the tensioning screw 303 causes the tensioning screw 303 to retract relative to the housing 307. The tensioning screw 303 is engaged with the clamping assembly 309 such that when the tensioning screw 303 is retracted relative to the housing 307, the clamping assembly 309 and the clamping screw 301 are also retracted. For example, a proximal surface 333 of the tensioning screw 303 can engage with a flange 335 of the clamping screw 301. The tensioning screw 303 can also be engaged with the clamping assembly 309 via internal threads (not shown). Accordingly, when the tensioning screw 303 is retracted from the housing 307, the proximal surface 333 of the tensioning screw contacts the flange 335 of the clamping screw 301, thereby causing the clamping screw 301 (and, correspondingly, the clamping assembly 309) to be retracted as well. As the clamping assembly 309 is clamped on the wire 205, retraction of the clamping assembly 309 increases tension in the wire 205.

In some embodiments, a spring 337 is disposed around the collet housing 311 between a distal flange 339 of the collet housing 311 and an engagement surface 341 of the interior surface 331. When compressed, this spring 337 urges the collet housing 311 (and, correspondingly, the clamping assembly 309) in a distal direction. This countervailing force provided by the spring 337 can provide for increased control in the amount of tension applied to the wire 205 during rotation of the tensioning screw 303. FIGS. 4A-4C illustrate side cross-sectional views of a second tensioner clamp 211 in accordance with some embodiments. The second tensioner clamp 211 is engaged with the wire 209 during different points of operation of the second tensioner clamp 211. In particular, FIG. 4A illustrates the second tensioner clamp 211 prior to clamping the wire 209, FIG. 4B illustrates the second tensioner clamp 211 after clamping the wire 209, and FIG. 4C illustrates the second tensioner clamp 211 after clamping and tensioning the wire 209.

The second tensioner clamp 211 can utilize many features similar to the first tensioner clamp 207 described above with respect to FIGS. 3A-3D, for example by providing combined clamping and tensioning capabilities. However, the particular configuration of the tensioner clamp 211 utilizes alternative mechanisms to clamp and to tension the wire 209 can differ.

Referring to FIG. 4A, the second tensioner clamp 211 includes an outer housing 407 surrounding a clamping assembly 409. The outer housing 407 can be configured to be fixedly coupled to a ring of a ring fixator. The clamping assembly 409 includes a clamp body 411 with a central opening 413 that receives the wire 209 therethrough. A radial aperture 415 in the clamp body 411 is oriented transversely with respect to the central opening 413. For example, in some embodiments the aperture 415 can be perpendicular to the central opening 413. A clamping screw 417 (e.g., a set screw) can be threadably engaged with the aperture 415 and configured to be rotated to apply downward pressure onto the wire 209, as illustrated in FIG. 4B. Rotation of the clamping screw 417 into this position can clamp the wire 209 into position with respect to the clamping assembly 409.

Referring to FIG. 4C, the second tensioner clamp 211 includes a tensioning nut 419 that is threadably engaged with the clamp body 411 such that rotation of the tensioning nut 419 causes the clamp body 411 to be retracted with respect to the housing 407, thereby applying tension to the wire 209. In some embodiments, the second tensioner clamp 211 further includes a spring 421 surrounding a portion of the clamp body 411 and configured to urge the clamp body 411 away from the tensioning nut 419 when the clamp body 411 is retracted with respect to the housing 407. This countervailing force provided by the spring 421 can provide for increased control in the amount of tension applied to the wire 205.

In operation, a first driver (not shown) can be used to rotate the clamping screw 417, which causes is the clamping screw 417 to be downwardly threaded through the aperture 415 until it presses upon the wire 209 with sufficient pressure to clamp the wire 209 in place. A second driver (not shown) can then be used to rotate the tensioning nut 419, which causes tension to be applied to the wire 209. The tensioning nut 419 can be rotated to gradually increase and decrease the applied tension to the wire 209. The tensioning nut 419 can be rotated until the desired tension is applied to the wire 209. Rotation of the tensioning nut 419 in the opposite direction causes tension to be reduced on the wire 209. In other embodiments, a single driver can be used to control both the clamping screw 417 and the tensioning nut 419, thereby reducing the need for two separate drivers. In other embodiments, a single instrument can house a first driver for operating the clamping screw 417 and a second driver for operating the tensioning nut 419, thereby advantageously allowing a single instrument to perform both clamping and tensioning.

Often times, when attaching a ring fixator to a patient, one individual must hold a ring, while another extends the wires through the patient. Without an individual holding the ring, the ring fixator can slip and become disengaged during application. It has been found that providing a ring with a soft tissue spacer formed therein can help to retain the ring on the patient. The soft tissue spacer is advantageously designed to be removable such that once the ring of the ring fixator is put in place, it can be removed. By providing such a soft tissue spacer, this reduces the reliance on an individual having to hold the ring during installation of the ring fixator.

Figure 5:
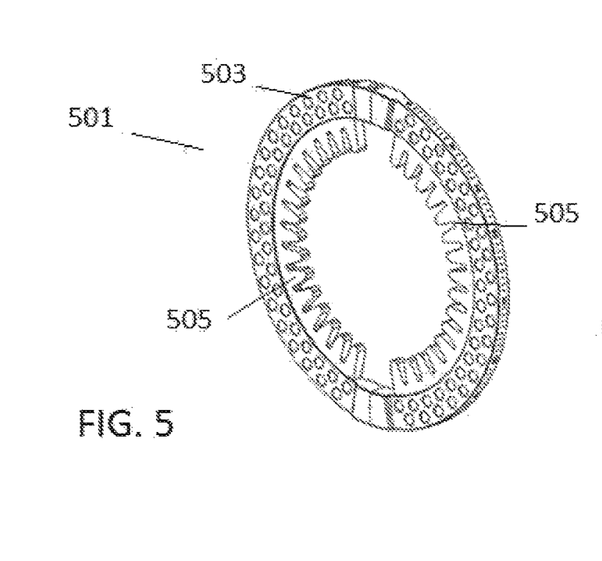
FIG. 5 illustrates a ring fixator with a soft tissue spacer in accordance with an embodiment of the present technology.

FIG. 5 illustrates a perspective view of a ring fixator 501 having a ring 503 and a spacer 505 coupled to the ring. The spacer 505 coupled to the ring can alleviate the need to rely on someone to hold the ring during installation. In some embodiments, the spacer 505 can be made of foam or other soft material, and can extend radially inwardly from the ring 503 so as to engage the anatomy of the patient. Providing a ring 503 with a soft tissue spacer 505 formed therein advantageously reduces the need to have an additional person hold the ring in place while applying the ring fixator. In addition, as the spacer 505 is formed of a soft material (e.g., foam), this provides added comfort to a patient during installation. The soft tissue spacer 505 can be removable such that once the ring fixator 501 is put in place, the spacer 505 can be removed. The soft tissue spacer 505 can be attached to the ring 503 via an adhesive or via nubs/protrusions that are insertable into openings in the ring. In some embodiments, the spacer 505 can be attached to the ring via an adhesive or via nubs/protrusions that are insertable into openings in the ring, thereby making it easy to attach and remove the spacer 505 from the ring.

As shown in FIG. 5, one or more spacers 505 can be attached to different segments of the inner wall of a ring. In the present embodiment, a first spacer is attached to one side of the ring, while a second spacer is attached to a second side of the ring. By providing a first spacer that is independent from a second spacer, this facilitates ease of attachment of the spacers within the ring. In addition, as shown in FIG. 5, each of the spacers can include recesses. These recesses can be in contact with the patient, and can advantageously help to accommodate varying patient anatomy.

Often times, a ring of a ring fixator (e.g., composed of two half circles) can be attached to a patient via bolts or screws. As the ring fixator is composed of multiple rings, it can be time consuming to perform the operation. It has been found that it is possible to reduce the time of the operation by providing various quick-connect mechanisms that allow a ring of a ring fixator to be attached to a patient quickly.

Figure 6:
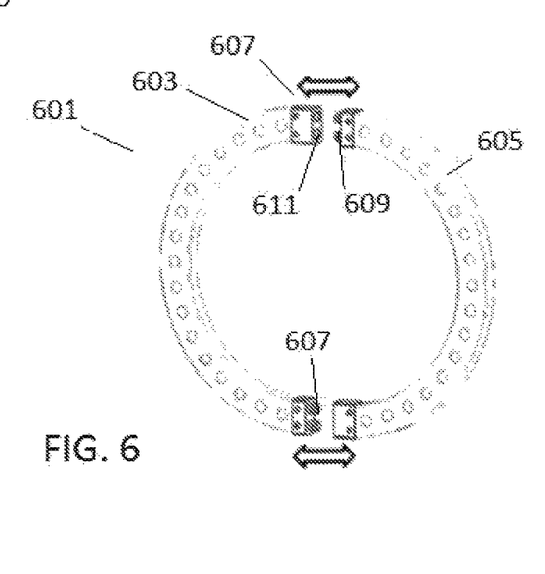
FIG. 6 illustrates a ring fixator with quick-connect segments in accordance with an embodiment of the present technology.

FIG. 6 illustrates a ring 601 having first and second members 603 and 605 joined by quick-connect components 607. The quick-connect components 607 shown in FIG. 6 advantageously allow the first and second members 603 and 605 to be secured together quickly. In the illustrated embodiment, the quick-connect components 607 include pins 609 and corresponding recesses 611 to receive the pins 609 therein. The quick-connect components 607 can take various other forms, such as mateable notches and protrusions, grooves and nubs, etc. In some embodiments, the quick-connect components 607 can include magnetic holding features in addition to or in lieu of mechanical mating features. In some embodiments, the two members 603 and 605 can be connected using these quick connect components 607 in addition to traditional screws, thereby forming a way to rapidly secure the two members 603 and 605 together while initially applying the ring fixator to a patient, while still allowing for a more robust fixation to be applied at a later stage through the use of screws.

Although many of the embodiments are described above with respect to devices, systems, and methods for ring fixators, other embodiments are within the scope of the present technology. Additionally, other embodiments of the present technology can have different configurations, components, and/or procedures than those described herein. For example, other embodiments can include additional elements and features beyond those described herein, or other embodiments may not include several of the elements and features shown and described herein. In particular, the ring fixators can be combined and used with other types of fixators, including rod fixators. In addition, the ring fixators can be used with various components used to heal bone fractures, including but not limited to, plates, rods, and screws.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the invention have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A ring fixator assembly comprising:
   a ring configured to surround a bone;
   a retention device disposed at a first position on the ring;
   a tensioner clamp disposed at a second position on the ring; and
   a wire extending between the retention device and the tensioner clamp,
   wherein the tensioner clamp comprises a housing including a clamping member therein configured to secure the wire in position with respect to the tensioner clamp and a tensioning member configured to apply tension to the wire, wherein rotation of the tensioning member causes the tensioning member to retract away from the housing, thereby causing tension on the wire.

2. The ring fixator assembly of claim 1, wherein the clamping member comprises a clamping screw and wherein the tensioning member comprises a tensioning screw, and wherein the clamping screw and the tensioning member are configured to be controlled by a single driver.

3. The ring fixator assembly of claim 1, wherein the housing surrounds a clamping assembly, the clamping assembly comprising:
   a collet housing; and
   a collet received at least partially within the collet housing,
   wherein the wire passes through a central opening in the collet,
   wherein the clamping member comprises a clamping screw threadably engaged with the collet such that rotation of the clamping screw causes the collet to be drawn into the collet housing, thereby clamping the wire, and
   wherein the tensioning member comprises a tensioning screw threadably engaged with the housing and coupled to the clamping assembly such that rotation of the tensioning screw causes the clamping assembly to be drawn away from the retention device, thereby applying tension to the wire.

4. The ring fixator assembly of claim 3, wherein the collet comprises a compressible end portion that compresses when drawn into the collet housing, thereby clamping the wire.

5. The ring fixator assembly of claim 3, wherein the tensioning screw is coaxial with the clamping screw.

6. The ring fixator assembly of claim 1, wherein the ring comprises:
   a first ring portion;
   a second ring portion; and
   a quick-connect assembly that releasably couples the first ring portion to the second ring portion.

7. The ring fixator assembly of claim 6, wherein the quick-connect assembly comprises first magnetic features disposed on ends of the first ring portion and second magnetic features disposed on ends of the second ring portion, the first and second magnetic features configured to be magnetically joined together.

8. The ring fixator assembly of claim 1, further comprising a spacer coupled to the ring and extending radially inwardly from the ring, the spacer configured to engage a patient's anatomy when the ring is positioned around a patient's limb.

9. A ring fixator assembly comprising:
   a tensioner clamp, wherein the tensioner clamp comprises:
      a central passage configured to receive a wire therein;
      a housing including a clamping member configured to secure the wire in position within the central passage; and
      a tensioning member configured to apply tension to the wire after the clamping member has secured the wire in position, wherein rotation of the tensioning member causes the tensioning member to retract away from the housing, thereby causing tension on the wire.

10. The ring fixator assembly of claim 9, wherein the clamping member comprises a clamping screw and wherein the tensioning member comprises a tensioning screw, and wherein the clamping screw and the tensioning screw are configured to be controlled by a single driver.

11. The ring fixator assembly of claim 9, wherein the housing surrounds a clamping assembly, the clamping assembly comprising:
   a collet housing; and
   a collet received at least partially within the collet housing,
   wherein the wire passes through a central opening in the collet,
   wherein the clamping member comprises a clamping screw threadably engaged with the collet such that rotation of the clamping screw causes the collet to be drawn into the collet housing, thereby clamping the wire.

12. The ring fixator assembly of claim 11, wherein the tensioning member comprises a tensioning screw threadably engaged with the housing and coupled to the clamping assembly such that rotation of the tensioning screw causes the clamping assembly to be drawn away from the retention device, thereby applying tension to the wire.

13. The ring fixator assembly of claim 11, wherein the collet comprises a compressible end portion that compresses when drawn into the collet housing, thereby clamping the wire.

14. The ring fixator assembly of claim 13, wherein the compressible end portion comprises flared portions separated by gaps.

15. The ring fixator assembly of claim 11, wherein the tensioning screw is coaxial with the clamping screw.

* * * * *